(12) United States Patent
Matsubara et al.

(10) Patent No.: US 11,518,982 B2
(45) Date of Patent: Dec. 6, 2022

(54) METHOD FOR MANUFACTURING MESENCHYMAL CELL LINE DERIVED FROM VERTEBRATE ANIMAL ADIPOSE TISSUE

(71) Applicant: AdipoSeeds, Inc., Tokyo (JP)

(72) Inventors: Yumiko Matsubara, Tokyo (JP); Yasuo Ikeda, Tokyo (JP); Keiichi Tozawa, Tokyo (JP); Hideyuki Saya, Tokyo (JP); Hiroyuki Nobusue, Tokyo (JP)

(73) Assignee: AdipoSeeds, Inc., Tokyo (JP)

( * ) Notice: Subject to any disclaimer, the term of this patent is extended or adjusted under 35 U.S.C. 154(b) by 366 days.

(21) Appl. No.: 15/779,578

(22) PCT Filed: Nov. 30, 2016

(86) PCT No.: PCT/JP2016/005016
§ 371 (c)(1),
(2) Date: May 29, 2018

(87) PCT Pub. No.: WO2017/094260
PCT Pub. Date: Jun. 8, 2017

(65) Prior Publication Data
US 2020/0190474 A1    Jun. 18, 2020

(30) Foreign Application Priority Data

Dec. 1, 2015 (JP) .............................. JP2015-234836

(51) Int. Cl.
C12N 5/00    (2006.01)
C12N 5/077    (2010.01)
C12N 5/0775    (2010.01)

(52) U.S. Cl.
CPC ......... *C12N 5/0653* (2013.01); *C12N 5/0667* (2013.01); *C12N 2506/1384* (2013.01)

(58) Field of Classification Search
None
See application file for complete search history.

(56) References Cited

U.S. PATENT DOCUMENTS

| | | | | |
|---|---|---|---|---|
| 8,835,165 | B2 * | 9/2014 | Prat .................... | G01N 33/5073 435/325 |
| 10,113,147 | B2 * | 10/2018 | Matsubara ............ | C12N 5/0644 |
| 10,729,726 | B2 * | 8/2020 | Garcia Castro ......... | A61P 43/00 |
| 2007/0110729 | A1 | 5/2007 | Kang et al. | |
| 2016/0177265 | A1 * | 6/2016 | Matsubara ............ | C12N 5/0644 435/377 |
| 2017/0151284 | A1 * | 6/2017 | Dalemans ............... | A61P 31/04 |

FOREIGN PATENT DOCUMENTS

| JP | 200083656 | 3/2000 |
|---|---|---|
| JP | 2009527221 | 7/2009 |
| JP | 5055611 | 8/2012 |
| WO | WO 02/06450 | 1/2002 |
| WO | 2014208100 | 12/2014 |
| WO | WO 2014208100 | * 12/2014 |
| WO | WO 2016001846 | * 1/2016 |

OTHER PUBLICATIONS

Matsubara Y.et al., Culture of megakaryocytes and platelets from subcutaneous adipose tissue and a preadipocyte cell line, Methods Mol.Biol., 2012,788,p. 249-58.*
Gimble et al., Stem Cells 2011;29:749-754 Concise Review: Adipose-Derived Stromal Vascular Fraction Cells and Stem Cells: Let's Not Get Lost in Translation.*
Sugihara et al ., Proliferation of unilocular fat cells in the primary culture Journal of Lipid Research vol. 28, 1987 pp. 1038-1045.*
Jumabay, Medet and Kristina I. Boström, "Dedifferentiated fat cells: A cell source for regenerative medicine," World J Stem Cells, 7(10: 1202-1214 (Nov. 26, 2015).
Peng et al., "Phenotupic and Functional Properties of Porcine Dedifferentiated Fat Cells During the Long-Term Culture in Vitro," Biomed Research International, vol. 2015, Article ID 673651, 10 pages, Jan. 2015.
Kou et al., "The phenotype and tissue-specific nature of multipotent cells derived from human mature adipocytes," Biochemical and Biophysical Research Communications, 444: 543-548 (2014).
Sousa et al., "Human Adult Stem Cells from Diverse Origins: An Overview from Multiparametric Immunophenotyping to Clinical Applications," Cytometry Part A: 85A: 43-77 (2014).
Notification of Transmittal of Translation of the International Preliminary Report on Patentability and the Translation of the International Preliminary Report on Patentability for International Application No. PCT/JP2016/005016 issued by the International Bureau of WIPO on Jun. 21, 2018, 6 pages.
Reems, Jo-Anna, Nicolas Pineault, and Sijie Sun. "In vitro megakaryocyte production and platelet biogenesis: state of the art." Transfusion medicine reviews 24, No. 1 (2010): 33-43.

(Continued)

*Primary Examiner* — Maria G Leavitt
(74) *Attorney, Agent, or Firm* — Occhiuti & Rohlicek LLP

(57) ABSTRACT

A method for producing a mesenchymal cell line derived from a vertebrate adipose tissue, and a mesenchymal cell line derived from a vertebrate adipose tissue produced by the method. Advantageously, a method for producing a mesenchymal cell line derived from a vertebrate adipose tissue is achieved more simply, in a shorter period of time, and more efficiently. Also, a mesenchymal cell line is derived from a vertebrate adipose tissue produced by the production method. The method for producing a mesenchymal cell line derived from a vertebrate adipose tissue comprises: (A) inducing differentiation of one or more cells selected from a stromal vascular fraction comprising a mesenchymal stem cell, an adipose progenitor cell, and a stromal cell of a vertebrate adipose tissue into a mature adipocyte; and (B) inducing dedifferentiation of the mature adipocyte obtained in step (A) to obtain a mesenchymal cell line derived from the vertebrate adipose tissue.

30 Claims, 6 Drawing Sheets

(56) References Cited

OTHER PUBLICATIONS

Takayama, Naoya, Hidekazu Nishikii, Joichi Usui, Hiroko Tsukui, Akira Sawaguchi, Takashi Hiroyama, Koji Eto, and Hiromitsu Nakauchi. "Generation of functional platelets from human embryonic stem cells in vitro via ES-sacs, VEGF-promoted structures that concentrate hematopoietic progenitors." Blood 111, No. 11 (2008): 5298-5306.

Nakamura, Sou, Naoya Takayama, Shinji Hirata, Hideya Seo, Hiroshi Endo, Kiyosumi Ochi, Ken-ichi Fujita et al. "Expandable megakaryocyte cell lines enable clinically applicable generation of platelets from human induced pluripotent stem cells." Cell stem cell 14, No. 4 (2014): 535-548.

Ono, Yukako, Yuhuan Wang, Hidenori Suzuki, Shinichiro Okamoto, Yasuo Ikeda, Mitsuru Murata, Mortimer Poncz, and Yumiko Matsubara. "Induction of functional platelets from mouse and human fibroblasts by p45NF-E2/Maf." Blood (2012): blood—2012.

Matsubara, Yumiko, Mitsuru Murata, and Yasuo Ikeda. "Culture of megakaryocytes and platelets from subcutaneous adipose tissue and a preadipocyte cell line." In Platelets and Megakaryocytes, pp. 249-258. Springer, New York, NY, 2012.

Matsubara, Yumiko, Emi Saito, Hidenori Suzuki, Naohide Watanabe, Mitsuru Murata, and Yasuo Ikeda. "Generation of megakaryocytes and platelets from human subcutaneous adipose tissues." Biochemical and biophysical research communications 378, No. 4 (2009): 716-720.

Matsubara, Yumiko, Hidenori Suzuki, Yasuo Ikeda, and Mitsuru Murata. "Generation of megakaryocytes and platelets from preadipocyte cell line 3T3-L1, but not the parent cell line 3T3, in vitro." Biochemical and biophysical research communications 402, No. 4 (2010): 796-800.

Fain, John N. "Release of Interleukins and Other Inflammatory Cytokines by Human Adipose Tissue Is Enhanced in Obesity and Primarily Due to the Nonfat Cells." Vitamins and Hormones, vol. 74, 2006, pp. 443-477., doi:10.1016/s0083-6729(06)74018-3.

\* cited by examiner

[Fig 1]
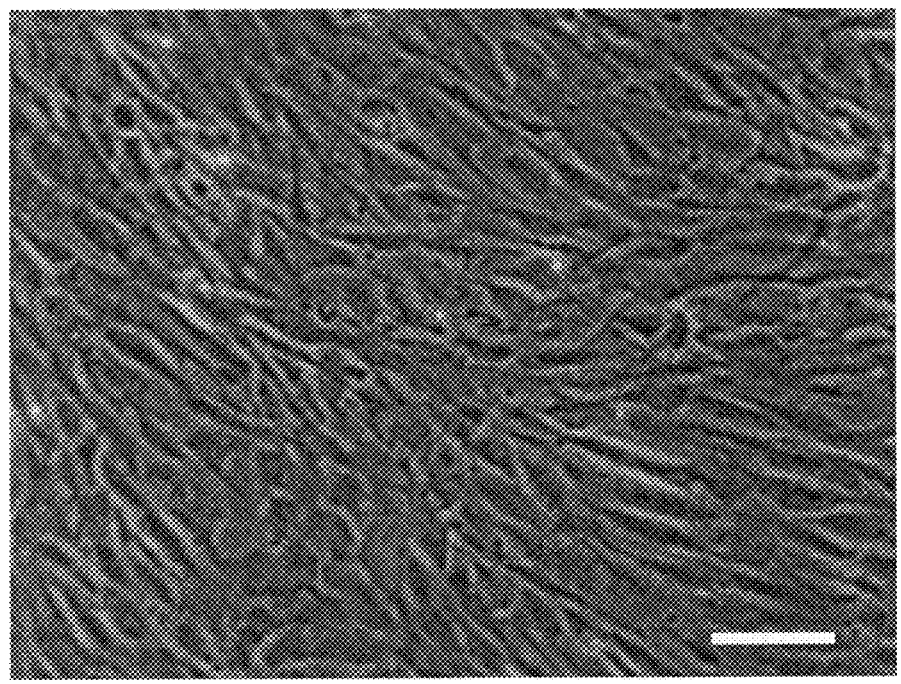

[Fig 2]
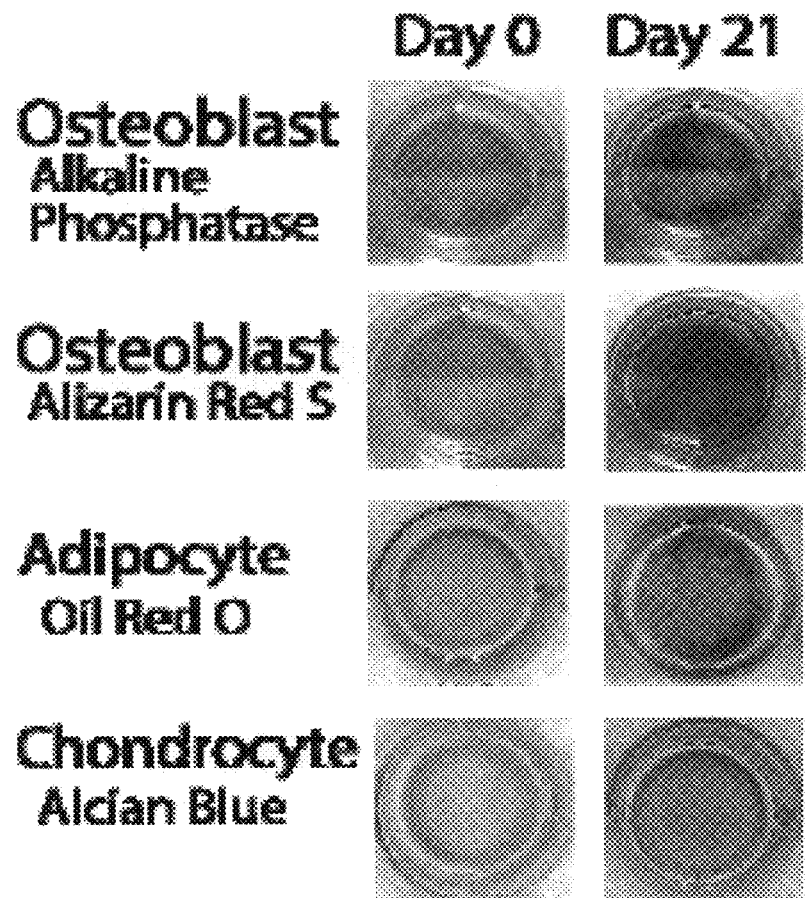
[Fig 3]
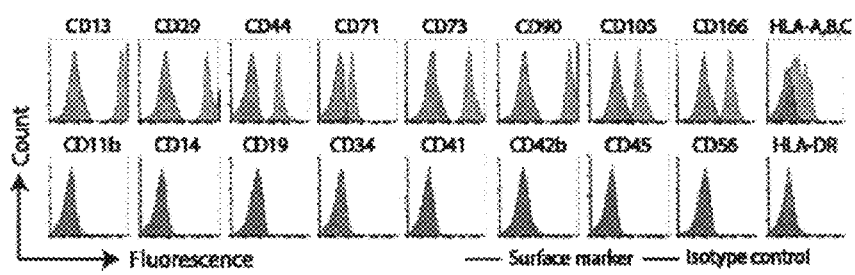

[Fig 4]
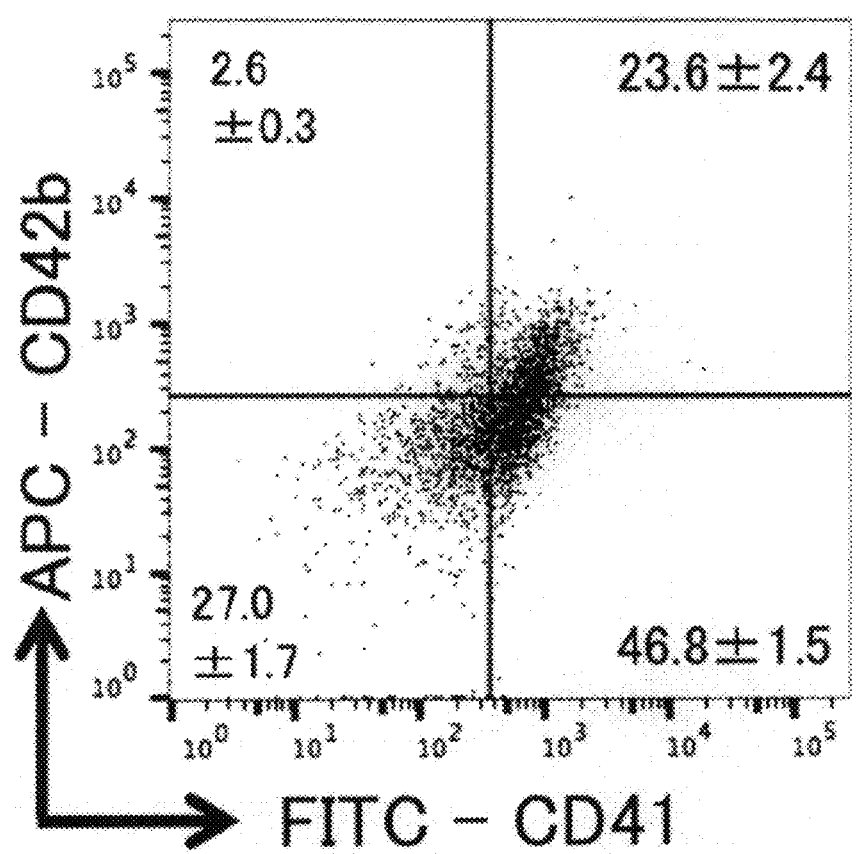

[Fig 5]
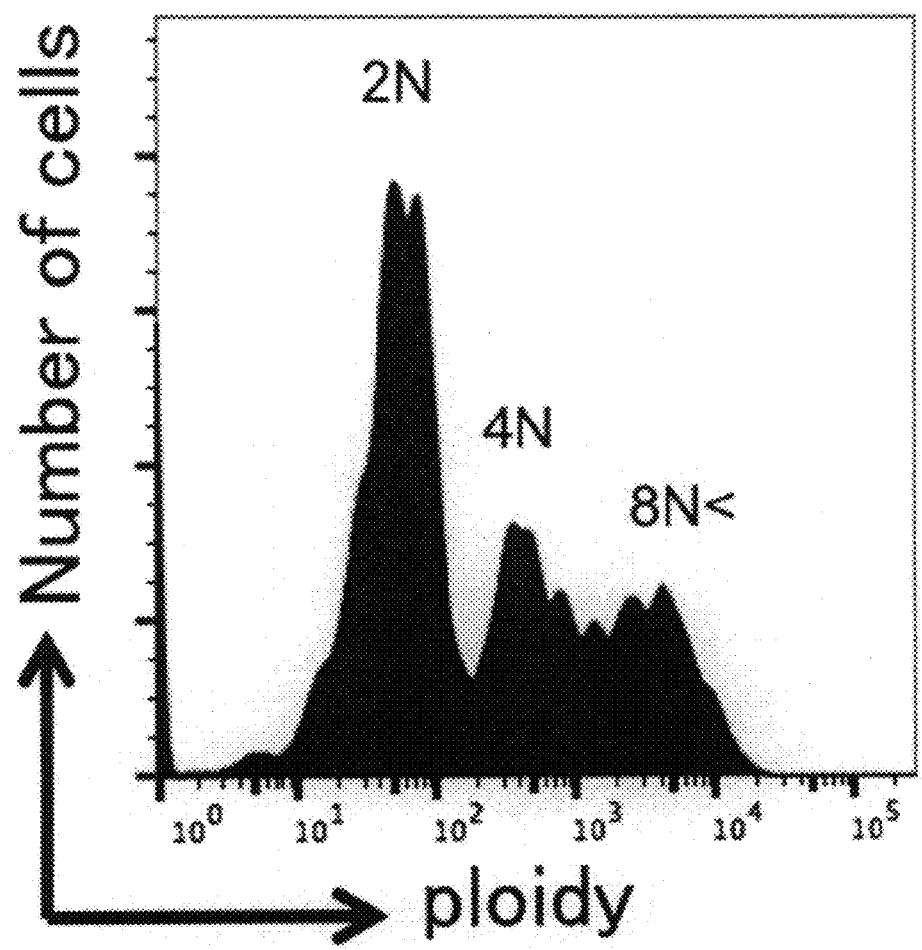

[Fig 6]
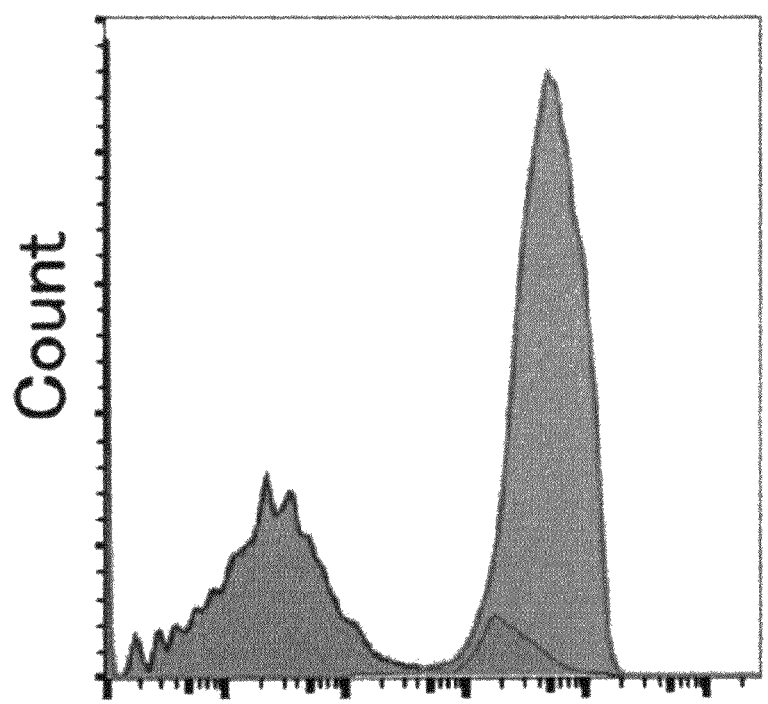

[Fig 7]
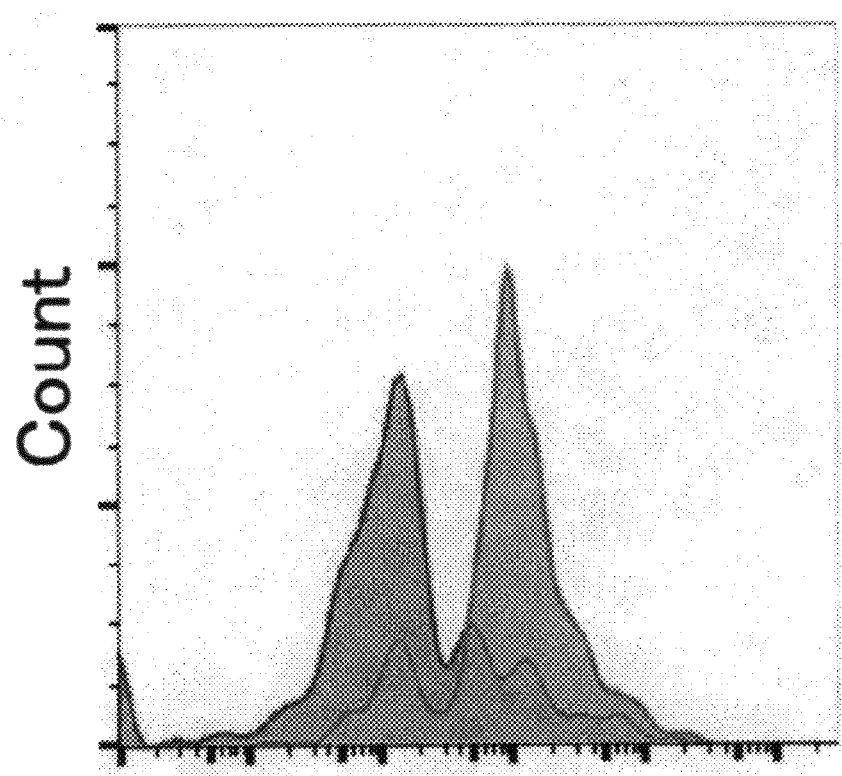

METHOD FOR MANUFACTURING MESENCHYMAL CELL LINE DERIVED FROM VERTEBRATE ANIMAL ADIPOSE TISSUE

CROSS REFERENCE TO RELATED APPLICATIONS

This application is a National Phase under 35 USC 371 of International Application No. PCT/JP2016/005016 filed Nov. 30, 2016, which claims priority to Japanese Application No. 2015-234836 filed Dec. 1, 2015, the contents of which are hereby incorporated by reference in their entirety.

TECHNICAL FIELD

The present invention relates to a method for producing a mesenchymal cell line derived from a vertebrate adipose tissue and a mesenchymal cell line derived from a vertebrate adipose tissue produced by the production method.

BACKGROUND ART

Platelet transfusion is the only treatment method on thrombocytopenia caused by bleeding associated with an accident or during use of an anticancer agent, and the platelet preparation used for such an instance relies 100% on blood donation of the good will at present. Platelets are extremely fragile and there has been no method available to enable a long term platelet preservation for the purpose of treatment. In reality, the shelf life of platelets is 4 days at the latest medical institutions but the substantial storage life at clinical sites including clinics is about 3 days when the time required for inspection and shipment is considered. Thus, many blood banks have been always challenged to keep platelets fresh and store, and further the supply of platelet preparation which relies on blood donation is susceptible to the decrease of blood donors and the increase of blood donors with virus infections.

Accordingly, the development of a new platelet supply source, which replaces with the blood donation posing such problems, has been drawing attentions in recent years (Non-patent Document 1). For example, there is a technological development for a large amount of platelet production outside the body utilizing hematopoietic stem cells (umbilical cord blood stem cells), which are somatic stem cells. However, a method for amplifying hematopoietic stem cells itself outside the body has not been established, which is thus not ready for practical use. To the contrary, embryonic stem (ES) cells, which are pluripotent stem cells, have a benefit of being unlimitedly proliferated outside the body and thus have been drawing attentions as a supply source for producing blood cells including platelets. In this regard, a technology has been already reported for producing mature megakaryocytes and platelets from human ES cells (Non-patent Document 2). However, the platelet production efficiency is poor in this method requiring tens of thousands of petri dishes for producing one batch of blood transfusion preparation, hence practically insufficient.

Platelet transfusion poses a problem of platelet transfusion refractoriness. Platelets having human leukocyte antigen (HLA) different from that of a patient can be used at the first time blood transfusion but a specific antibody to the HLA is produced in the body of the patient by repeated blood transfusions, whereby platelets transfused are rapidly rejected. Alternatively, platelets also have human platelet alloantigen (HPA), distinctive blood types, which also cause transfusion refractoriness due to the difference in the compatibility. A technology, which may overcome this problem, for producing megakaryocytes and platelets from human induced pluripotent stem (iPS) cells is reported (Non-patent Document 3). For example, platelets induced from patient-derived iPS cells enable, in theory, the preparation of a custom-made rejection-free platelet preparation. However, the platelet production using iPS cells requires about 50 days from fibroblasts to the platelet production (Non-patent Document 3), hence practically insufficient. To the contrary, a method is known for producing platelets from fibroblasts by a technique called a direct reprogramming (Non-patent Document 4). According to this technique, the period of time to the platelet production can be significantly cut shorter than the method involving iPS cells, rendering the benefit of reaching the platelet production in about 14 days. However, the direct reprogramming using fibroblasts requires gene transfection which thus raises a concern over the safety by the contamination of a gene transfection vector.

Separately, MKLI medium (megakaryocyte lineage induction medium) is known as a medium capable of inducing hematopoietic stem cells to differentiate into megakaryocytes and platelets. The MKLI medium is medium in which 2 mM of L-glutamine, 100 U/mL of a penicillin-streptomycin solution, 0.52 bovine serum albumin, 4 µg/mL of LDL cholesterol, 200 µg/mL of iron-saturated transferrin (iron-bound transferrin), 10 µg/mL of insulin, 50 µM of 2-β-mercaptoethanol, nucleotides (20 µM each of ATP, UTP, GTP and CTP), and 50 ng/mL of thrombopoietin (TPO) are added to Iscove's Modified Dulbecco's Medium (IMDM) (Non-patent Document 5). The present inventors have been so far proceeding the study on the technology for inducing cells other than hematopoietic stem cells to differentiate into megakaryocytes and platelets, and have found that human adipose progenitor cells derived from a subcutaneous adipose tissue (Non-patent Documents 5, 6) or mouse adipose progenitor cells (Non-patent Documents 5, 7) cultured in the above MKLI medium can be differentiated into megakaryocytes and platelets. The present inventors have further proceeded the study and found an outstanding method capable of producing megakaryocytes and/or platelets (Patent Document 1). The production method of Patent Document 1 is a production method wherein mesenchymal cells are cultured in basal medium for mesenchymal cell culture comprising iron ions and iron transporters and megakaryocytes and/or platelets are collected from the cultured product. The production method of Patent Document enables the production of megakaryocytes having the platelet-producing ability and/or platelets having the thrombus-forming ability from mesenchymal cells such as adipose progenitor cells outside the body without adding TPO and the like to the medium in a comparatively short period of time, simply, and in a large amount at a lower cost or more efficiently.

Thus, the production method of Patent Document 1 is the outstanding production method which overcame the drawbacks of the conventional platelet production method using hematopoietic stem cells, ES cells or iPS cells. Patent Document 1 discloses the use of an adipose progenitor cell line as a kind of the mesenchymal cells before induction of differentiation into megakaryocytes and platelets. Adipose progenitor cells are commercially available and can also be established from an adipose tissue. As a method for establishing an adipose progenitor cell line from an adipose tissue, a method is known wherein an adipose tissue is treated with collagenase to separate adipocytes, a cell suspension comprising the adipocytes is centrifuged, mature adipocytes in the supernatant are recovered, and the mature adipocytes are subjected to ceiling culture in medium comprising serum to establish a cell line (Patent Document 2). However, this cell line establishing method required a period of more than about 2 months and further required a technically skilled operation, hence leaving practical issues unsolved.

PRIOR ART DOCUMENTS

Patent Documents

Patent Document 1: International Publication No. WO 2014/208100
Patent Document 2: Japanese Patent No. 5055611

Non-Patent Documents

Non-patent Document 1: Reems J A, Pineault N, Sun S. In vitro megakaryocyte production and platelet biogenesis: state of the art. Transfus Med Rev. 2010; 24 (1): 33-43.
Non-patent document 2: Takayama N, Nishikii H, Usui J, et al. Generation of functional platelets from human embryonic stem cells in vitro via ES-sacs, VEGF-promoted structures that concentrate hematopoietic progenitors. Blood. 2008; 111 (11): 5298-5306.
Non-patent Document 3: Nakamura S, Takayama N, Hirata S, et al. Expandable Megakaryocyte Cell Lines Enable Clinically Applicable Generation of Platelets from Human Induced Pluripotent Stem Cells. Cell Stem Cell. 2014 February 12.pii: S1934-5909(14)00012-5. doi: 10.1016/j.stem.2014.01.011.
Non-patent Document 4: Ono Y, Wang Y, Suzuki H, et al. Induction of functional platelets from mouse and human fibroblasts by p45NF-E2/Maf. Blood. 2012; 120: 3812-3821.
Non-patent Document 5: Matsubara Y, Murata M, Ikeda Y. Culture of megakaryocytes and platelets from subcutaneous adipose tissue and a preadipocyte cell line. Methods Mol Biol. 2012; 788: 249-258.
Non-patent Document 6: Matsubara Y, Saito E, Suzuki H, Watanabe N, Murata M, et al. Generation of megakaryocytes and platelets from human subcutaneous adipose tissues. Biochem Biophys Res Commun. 2009; 378: 716-720.
Non-patent Document 7: Matsubara Y, Suzuki H, Ikeda Y, Murata M. Generation of megakaryocytes and platelets from preadipocyte cell line 3T3-L1, but not the parent cell line 3T3, in vitro. Biochem Biophys Res Commun. 2010; 402: 796-800.

SUMMARY OF THE INVENTION

Object to be Solved by the Invention

An object of the present invention is to provide a method for producing a mesenchymal cell line derived from a vertebrate adipose tissue, and a mesenchymal cell line derived from a vertebrate adipose tissue produced by the production method. More specifically, an object of the present invention is to provide a method for producing a mesenchymal cell line derived from a vertebrate adipose tissue more simply, in a shorter period of time, and more efficiently, and a mesenchymal cell line derived from a vertebrate adipose tissue produced by the production method.

Means to Solve the Object

The present inventors conducted extensive studies to solve the above problems. They found that by inducing dedifferentiation of mature adipocytes obtained by inducing differentiation of a cell population of a precipitate into mature adipocyte, which precipitate is obtained by centrifugation of a suspension comprising a cell population obtained by treating a vertebrate adipose tissue with an enzyme capable of dispersing the vertebrate adipose tissue cells, and not by inducing differentiation of a cell population (mature adipocytes) in the supernatant collected by said centrifugation, the dedifferentiation is caused in a high efficiency thus enabling to produce a mesenchymal cell line derived from a vertebrate adipose tissue more simply, in a shorter period of time, and more efficiently. The present invention has been thus completed. The method for producing a mesenchymal cell line derived from a vertebrate adipose tissue of the present invention, when compared with the method for producing an adipose progenitor cell line from an adipose tissue of Patent Document 2, had a less than half of the period for establishing the cell line and about 10 to 15 times the amount of the cell line established from the same amount of an adipose tissue.

Further, the present inventors found that the thus obtained mesenchymal cell line derived from a vertebrate adipose tissue can be suitable for long-term subculture and maintains proliferation potency and differentiation potency into mesodermal cells even after the long-term subculture, whereby the present invention was accomplished.

More specifically, the present invention relates to:
(1) a method for producing a mesenchymal cell line derived from a vertebrate adipose tissue, comprising the following steps (A) and (B):
(A) inducing differentiation of one or more cells selected from a stromal vascular fraction comprising a mesenchymal stem cell, an adipose progenitor cell, and a stromal cell of a vertebrate adipose tissue into a mature adipocyte; and
(B) inducing dedifferentiation of the mature adipocyte obtained in step (A) to obtain a mesenchymal cell line derived from the vertebrate adipose tissue,
(2) the method for producing a mesenchymal cell line derived from a vertebrate adipose tissue according to the above (1), wherein the one or more cells are a cell obtained by removing the mature adipocyte from a cell population obtained by treating the vertebrate adipose tissue with an enzyme capable of dispersing the vertebrate adipose tissue cells,
(3) the method for producing a mesenchymal cell line derived from a vertebrate adipose tissue according to the above (2), wherein the cell obtained by removing the mature adipocyte from the cell population obtained by treating the vertebrate adipose tissue with an enzyme capable of dispersing the vertebrate adipose tissue cells is a cell which is precipitated by centrifugation of a suspension comprising the cell population obtained by treating the vertebrate adipose tissue with an enzyme capable of dispersing the vertebrate adipose tissue cells,
(4) the method for producing a mesenchymal cell line derived from a vertebrate adipose tissue according to any one of the above (1) to (3), wherein the step of inducing differentiation of one or more cells into a mature adipocyte in step (A) is a step of culturing the one or more cells in basal medium for mesenchymal cell culture comprising one or more adipose cell differentiation inducing substances selected from the group consisting of dexamethasone, isobutylmethylxanthine, insulin, and serum,
(5) the method for producing a mesenchymal cell line derived from a vertebrate adipose tissue according to any one of the above (1) to (4), wherein inducing dedifferentiation of the mature adipocyte in step (B) is to perform ceiling culture of the mature adipocyte,
(6) the method for producing a mesenchymal cell line derived from a vertebrate adipose tissue according to any one of the above (2) to (5), wherein the enzyme capable of dispersing the vertebrate adipose tissue cells is one or more enzymes selected from the group consisting of collagenase, trypsin, caseinase, clostripain, trypsin-EDTA, dispase, thermolysin, pronase, hyaluronidase, pancreatin, elastase, and papain,
(7) the method for producing a mesenchymal cell line derived from a vertebrate adipose tissue according to any one of the above (1) to (6), wherein the vertebrate is a mammal, and
(8) the method for producing a mesenchymal cell line derived from a vertebrate adipose tissue according to any one of the above (1) to (7), wherein the adipose tissue is a subcutaneous adipose tissue.

Further, the present invention relates to:
(9) a mesenchymal cell line derived from a vertebrate adipose tissue produced by the production method of any one of the above (1) to (8),
(10) the mesenchymal cell line derived from a vertebrate adipose tissue according to the above (9), wherein the mesenchymal cell line has a differentiation potency into one or more selected from the group consisting of a megakaryocyte/platelet, an osteoblast, a cartilage, and an adipocyte,
(11) the mesenchymal cell line derived from a vertebrate adipose tissue according to the above (9) or (10), wherein the mesenchymal cell line expresses one or more surface markers selected from the following surface marker group of mesenchymal cells, and does not express one or more surface markers selected from the following surface marker group of blood cells:
surface marker group of mesenchymal cells: CD13, CD29, CD44, CD71, CD73, CD90, CD105, CD166, HLA-ABC;
surface marker group of blood cells: CD11b, CD14, CD19, CD34, CD41, CD42b, CD45, CD56, HLA-DR, and
(12) the mesenchymal cell line derived from a vertebrate adipose tissue according to any one of the above (9) to (11), wherein the mesenchymal cell line has a differentiation inducing efficiency into a mesodermal cell which is 1.5 or more times more than that of a mesenchymal cell line derived from a vertebrate adipose tissue obtained by inducing dedifferentiation of a mature adipocyte collected from a vertebrate adipose tissue.

Furthermore, the present invention relates to:
(13) a method for producing a mesodermal cell, comprising a step of inducing differentiation of the mesenchymal cell line derived from a vertebrate adipose tissue according to any one of the above (9) to (12) into a mesodermal cell, to thereby obtain a mesodermal cell, and
(14) the method for producing a mesodermal cell according to the above (13), wherein the mesodermal cell is a megakaryocyte/platelet, an osteoblast, a cartilage, or an adipocyte.

Effect of the Invention

According to the present invention, a method for producing a mesenchymal cell line derived from a vertebrate adipose tissue, and a mesenchymal cell line derived from a vertebrate adipose tissue produced by the production method can be provided. More specifically, the present invention can provide a method for producing a mesenchymal cell line derived from a vertebrate adipose tissue more simply, in a shorter period of time, and more efficiently, and a mesenchymal cell line derived from a vertebrate adipose tissue produced by the production method.

Such a mesenchymal cell line has differentiation and proliferation potency maintained semipermanently, and thus has "a benefit of enabling to obtain the material for mesodermal cells in a larger amount" and "a benefit of immediately starting the production of mesodermal cells if a mesenchymal cell line is cryopreserved when mesodermal cells such as megakaryocytes, platelets, osteoblasts, cartilages, and adipocytes are needed. For this reason, the use of the mesenchymal cell line derived from a vertebrate adipose tissue of the present invention enables to obtain mesodermal cells in a shorter period of time and in a larger amount, whereby the meaning of the present invention on the cell therapy field which uses mesodermal cells is significant.

BRIEF DESCRIPTION OF DRAWINGS

FIG. 1 A drawing shows the observation result of the mesenchymal cell line derived from a human adipose tissue produced in Example 1 using a phase-contrast microscopy. The bar in FIG. 1 is 100 μm.

FIG. 2 Drawings show the investigation results on whether the mesenchymal cell line derived from a human adipose tissue produced in Example 1 has differentiation potency into osteoblasts, adipocytes, and chondrocytes.

FIG. 2, both panels in the first row from the top: the drawings show the confirmation results on whether cells of a human adipose tissue-derived mesenchymal cell line cultured to induce differentiation into osteoblasts for 21 days (Day 21) or a mesenchymal cell line derived from a human adipose tissue before induction of differentiation (Day 0) have an alkaline phosphatase activity, which is one of the characteristics of osteoblasts, by adding the substrate thereof (bromochloroindolyl phosphate/nitro blue tetrazolium). On Day 0 (left panel), the color development indicating the alkaline phosphatase activity (bluish purple color in reality but appeared as a blackish color in the drawing) is not substantially recognized but on Day 21 (right panel), the color development appears more intense than Day 0. FIG. 2, both panels in the second row from the top: the drawings show the confirmation results on whether cells of a human adipose tissue-derived mesenchymal cell line cultured to induce differentiation into osteoblasts for 21 days (Day 21) or a mesenchymal cell line derived from a human adipose tissue before induction of differentiation (Day 0) shows cell calcification, which is one of the characteristics of osteoblasts, by staining with Alizarin red. On Day 0 (left panel), the color development indicating the calcification of cells (red color in reality but appeared as a blackish color in the drawing) is not substantially recognized but on Day 21 (right panel), the color development appears more intense than Day 0. FIG. 2, both panels in the third row from the top: the drawings show the confirmation results on whether cells of a human adipose tissue-derived mesenchymal cell line cultured to induce differentiation into adipocytes for 21 days (Day 21) or a mesenchymal cell line derived from a human adipose tissue before induction of differentiation (Day 0) has fat globules, which is one of the characteristics of adipocytes, by staining with oil red O. On Day 0 (left panel), the color development indicating fat globules (red color in reality but appeared as a blackish color in the drawing) is not substantially recognized but on Day 21 (right panel), the color development appears more intense than Day 0. FIG. 2, both panels in the bottom row: the drawings show the confirmation results on whether cells of a human adipose tissue-derived mesenchymal cell line cultured to induce differentiation into chondrocytes for 21 days (Day 21) or a mesenchymal cell line derived from a human adipose tissue before induction of differentiation (Day 0) has extracellular matrix, which is distinctive in chondrocytes, by staining with Alcian blue. On Day 0 (left panel), the color development indicating the presence of extracellular matrix (blue color in reality but appeared as a blackish color in the drawing) distinctive in chondrocytes is not substantially recognized but on Day 21 (right panel), the color development appears more intense than Day 0.

FIG. 3 Drawings show the analysis results by the flow cytometry method on the expressions of the surface markers of mesenchymal cells and blood cells in the human adipose tissue-derived mesenchymal cell line produced in Example 1. Nine panels in the upper row show the results on the surface markers of mesenchymal cells (CD13, CD29, CD44, CD71, CD73, CD90, CD105, CD166, HLA-ABC), and nine panels in the lower row show the results on the surface markers of blood cells (CD11b, CD14, CD19, CD34, CD41, CD42b, CD45, CD56, HLA-DR). Nine panels in the upper row respectively have mostly two signal peaks, and each of the left peaks shows the result obtained by using a negative control antibody and each of the right peaks shows the result obtained by using an antisurface marker antibody.

FIG. 4 A drawing shows the fluorescence measurement result by the flow cytometry method on the cell population obtained by culturing a mesenchymal cell line derived from a human adipose tissue in MKLI medium for 7 days and labeling with fluorescent-labeled CD41 antibody and fluorescent-labeled anti-CD42b antibody. The abscissa shows the fluorescence intensity of the fluorescent-labeled CD41 antibody and the ordinate shows the fluorescence intensity of the fluorescent-labeled anti-CD42b antibody.

FIG. 5 A drawing showing the measurement result of flow cytometry on the PI fluorescence intensity of each cell after staining nucleus of the cell population obtained by culturing a mesenchymal cell line derived from a human adipose tissue in MKLI medium for 7 days with propidium iodide (PI). The abscissa shows the PI fluorescence intensity, and the ordinate shows the number of cells.

FIG. 6 A drawing shows the fluorescence measurement result by the flow cytometry method on the cell population obtained by culturing a mesenchymal cell line derived from a human adipose tissue in MKLI medium for 7 days and labeling with fluorescent-labeled anti-fibrinogen antibody (right peak in the drawing). Additionally, the drawing also shows the fluorescence measurement result by the flow cytometry method on a human adipose tissue-derived mesenchymal cell line labeled with fluorescent-labeled anti-fibrinogen antibody (left peak in the drawing). The abscissa shows the fluorescence intensity, and the ordinate shows the number of cells.

FIG. 7 A drawing showing the fluorescence measurement result by the flow cytometry method on the cell population obtained by culturing a mesenchymal cell line derived from a human adipose tissue in MKLI medium for 7 days and labeling with fluorescent-labeled anti-PAC-1 antibody (right peak in the drawing). Additionally, the drawing also shows the fluorescence measurement result by the flow cytometry method on a human adipose tissue-derived mesenchymal cell line labeled with fluorescent-labeled anti-PAC-1 antibody (left peak in the drawing). The abscissa shows the fluorescence intensity, and the ordinate shows the number of cells.

MODE OF CARRYING OUT THE INVENTION

<Method for Producing Mesenchymal Cell Line Derived from Vertebrate Adipose Tissue>

The method for producing a mesenchymal cell line derived from a vertebrate adipose tissue of the present invention (hereinafter simply referred to as "method for producing a cell line of the present invention") is not particularly limited as long as a method has;
(A) a step of inducing differentiation of one or more cells selected from a stromal vascular fraction comprising a mesenchymal stem cell, an adipose progenitor cell, and a stromal cell of a vertebrate adipose tissue into a mature adipocyte; and
(B) a step of inducing dedifferentiation of the mature adipocyte obtained in step (A) to obtain a mesenchymal cell line derived from the vertebrate adipose tissue.

The mature adipocyte obtained by the differentiation induction in step (A) is a mature adipocyte more easily dedifferentiated (hereinafter also referred to as "easy-to-dedifferentiate mature adipocyte" in the present Description) than a mature adipocyte which has been present in a vertebrate adipose tissue, and thus the dedifferentiation induction in step (B) presumably enables the production (establishment) of a mesenchymal cell line derived from a vertebrate adipose tissue more simply, in a shorter period of time, and more efficiently. The production method can be an ex vivo or in vitro production method.

(Step A)

The above step (A) is not particularly limited as long as it is a step of inducing differentiation of one or more cells (hereinafter also referred to as "mesenchymal stem cells" in the present Description) selected from a stromal vascular fraction comprising a mesenchymal stem cell, an adipose progenitor cell, and a stromal cell of a vertebrate adipose tissue into a mature adipocyte. The step of differentiation induction is an ex vivo or in vitro step of differentiation induction.

The species from which the adipose tissue is derived is not particularly limited as long as a species is a vertebrate, and examples include a mammal, a bird, a reptile, an amphibian, and a fish, of which a mammal such as a human, a mouse, a rat, a guinea pig, a rabbit, a cat, a dog, a horse, a cow, a monkey, a sheep, a goat, and a pig being preferable, of which a human being particularly preferable. Further, when the vertebrate adipose tissue-derived mesenchymal cell line produced by the method for producing a cell line of the present invention or mesodermal cells induced to differentiate from the cell line are administered or transplanted to vertebrate species, it is preferable to use the adipose tissue of the vertebrate species in the method for producing a cell line of the present invention in light of avoiding a rejection reaction.

The "adipose tissue" as used herein is not particularly limited as long as a tissue comprises fats and examples include a subcutaneous adipose tissue, an adipose tissue in the bone marrow, and a visceral adipose tissue, with a subcutaneous adipose tissue being preferable in light of comparatively low invasiveness to a vertebrate supplying the adipose tissue and being comparatively easily collectable.

The "stromal vascular fraction" as used herein means the cells other than mature adipocytes among the cells of a vertebrate adipose tissue. A stromal vascular fraction typically comprises cells such as a mesenchymal stem cell, an adipose progenitor cell, a stromal cell, a vascular endothelial cell, a cell related to blood, a smooth muscle cell, and a fibroblast. The "stromal vascular fraction" can be obtained by removing mature adipocytes from a cell population obtained by treating a vertebrate adipose tissue with an enzyme capable of dispersing the vertebrate adipose tissue cells.

The above "one or more cells selected from a stromal vascular fraction comprising a mesenchymal stem cell, an adipose progenitor cell, and a stromal cell of a vertebrate adipose tissue" are not limited as long as one or more cells are selected from a stromal vascular fraction comprising a mesenchymal stem cell, a preadipocyte or an adipose progenitor cell, and a stromal cell of a vertebrate adipose tissue, but in light of more efficiently producing a mesenchymal cell line derived from a vertebrate adipose tissue, the cell population, rather than comprising only an adipose progenitor cell, preferably comprises at least an adipose progenitor cell and a mesenchymal stem cell and/or a stromal cell, with the cell population comprising at least an adipose progenitor cell, a mesenchymal stem cell, and a stromal cell being more preferable, with the cell population of a stromal vascular fraction being further preferable in light of easy preparation.

Further, examples of the preferable embodiment of the above "one or more cells selected from a stromal vascular fraction comprising a mesenchymal stem cell, an adipose progenitor cell, and a stromal cell of a vertebrate adipose tissue" include one or more cells selected from a stromal vascular fraction comprising a mesenchymal stem cell, an adipose progenitor cell, and a stromal cell obtained by dispersing cells of the vertebrate adipose tissue, of which a cell population (cell population A) obtained by removing mature adipocytes from a cell population obtained by treating the vertebrate adipose tissue with an enzyme capable of dispersing the vertebrate adipose tissue cells is preferable. A cell population obtained by further removing vascular endothelial cells and/or cells related to blood from the cell population A may also be used. The above cell population (cell population A) obtained by removing mature adipocytes from a cell population obtained by treating a vertebrate adipose tissue with an enzyme capable of dispersing the vertebrate adipose tissue cells is a cell population of stromal vascular fractions, which typically comprises cells such as a mesenchymal stem cell, an adipose progenitor cell, a stromal cell, a vascular endothelial cell, a cell related to blood, a smooth muscle cell and a fibroblast of a vertebrate adipose tissue.

Examples of the above "treating a vertebrate adipose tissue with an enzyme capable of dispersing vertebrate adipose tissue cells" include a method in which a vertebrate adipose tissue is immersed in a solution comprising such an enzyme and incubated, for example, for about 30 minutes to 3 hours.

The above "enzyme capable of dispersing vertebrate adipose tissue cells" is not particularly limited as long as it can disperse cells of a vertebrate adipose tissue when allowed to act on the vertebrate adipose tissue, and examples include one or more enzymes selected from the group consisting of collagenase, trypsin, caseinase, clostripain, trypsin-EDTA, dispase, thermolysin, pronase, hyaluronidase, pancreatin, elastase, and papain, of which at least one or more enzymes selected from the group consisting of collagenase, trypsin, caseinase, and clostripain being preferable, and commercial collagenase (type I) and collagenase (type II) being more preferable, with collagenase (type II) being further preferable. Further, the above "enzyme capable of dispersing vertebrate adipose tissue cells" preferably comprises at least collagenase.

The above "removing mature adipocytes from a cell population obtained by treating a vertebrate adipose tissue with an enzyme capable of dispersing the vertebrate adipose tissue cells" is not particularly limited as long as a method can remove mature adipocytes from such a cell population, but examples preferably include a method of recovering a cell population (cell pellet) which is precipitated by centrifugation of a suspension comprising the above cell population. Mature adipocytes comprise a large amount of fats, thus have a light specific Gravity and float in the upper part of supernatant when centrifuged, hence the recovery of a cell pellet precipitated by the centrifugation enables the removal of mature adipocytes. Further, the method for removing vascular endothelial cells, smooth muscle cells, and fibroblasts from the cell population obtained by treating a vertebrate adipose tissue with an enzyme capable of dispersing vertebrate adipose tissue cells is not particularly limited as long as a method can remove these cells from such a cell population and examples include a method for removing vascular endothelial cells from the cell population when CD31 known as a surface marker of the vascular endothelial cell selects negative cells (or CD31 removes positive cells), and examples of the method for removing cells related to blood include a method for removing cells related to blood from the cell population by selecting CD45- (a surface marker of hematopoietic cells other than red blood cell and platelet) negative and Ter119- (a surface marker of red blood cell and progenitor cell thereof) negative cells (or CD45-positive and Ter119-positive cells are removed). Additionally, when 7-amino-actinomycin D (7-AAD), which is not a surface marker, being negative is used as an indicator, it is preferable because dead cells comprised in a vertebrate adipose tissue can be excluded. 7-AAD intercalates with a DNA chain of a dead cell and produces red fluorescence at a 488-nm excitation light.

The above precipitated cell pellet (cell population A) is cells of a stromal vascular fraction, which typically comprises a mesenchymal stem cell, an adipose progenitor cell, a stromal cell (a stroma cell), a vascular endothelial cell, a smooth muscle cell, and a fibroblast, however, those of which can differentiate into a mature adipocyte are a mesenchymal stem cell, an adipose progenitor cell, and a stromal cell. For this reason, a further step may or may not be included for removing any one or more, or all kinds, of the cells other than these 3 kinds from the above precipitated cell pellet before differentiation induction into a mature adipocyte is carried out, but it is preferable not to include such a step in light of convenience of operation. A vascular endothelial cell, a smooth muscle cell, and a fibroblast do not differentiate into a mature adipocyte even when induced with mesenchymal stem cells to differentiate into a mature adipocyte, or do not interfere in the differentiation of mesenchymal stem cells into mature adipocytes.

In the above step (A), examples of the method for inducing differentiation of one or more cells selected from a stromal vascular fraction comprising a mesenchymal stem cell, an adipose progenitor cell, and a stromal cell of a vertebrate adipose tissue into a mature adipocyte preferably include a method for culturing the one or more cells selected from a stromal vascular fraction comprising a mesenchymal stem cell, an adipose progenitor cell, and a stromal cell of a vertebrate adipose tissue in basal medium for mesenchymal cell culture comprising adipose cell differentiation inducing substances. The method for culturing mesenchymal stem cells in basal medium for mesenchymal cell culture comprising adipose cell differentiation inducing substances is not particularly limited as long as a method can induce differentiation of mesenchymal cells into mature adipocytes by such a culture, and the same method as the typical method for inducing differentiation of an adipose progenitor cell into a mature adipocyte, that is, a method for culturing a starting cell in basal medium for mesenchymal cell culture comprising adipose cell differentiation inducing substances can be used.

In the above step (A), examples of the conditions for culturing mesenchymal stem cells in basal medium for mesenchymal cell culture comprising adipose cell differentiation inducing substances include a method of adhesion culture in a culture vessel coated with the extracellular matrix, and examples of the culture temperature include typically a range from 12 to 45° C., preferably a range from 15 to 37° C., and examples of the culture period include, in light of the balance between producing a mesenchymal cell line derived from a vertebrate adipose tissue more efficiently and producing in a shorter period of time, a range from 5 to 16 days, preferably a range from 7 to 14 days, more preferably a range from 8 to 12 days, further preferably a range from 9 to 11, more preferably for 10 days. In the culture, mesenchymal stem cells may or may not be subcultured. Further, examples of the above extracellular matrix include at least one or more components selected from collagen, fibronectin, proteoglycan, and laminin, and BD Matrigel (registered trademark) (manufactured by BD Biosciences) comprising these components can also be used.

The above adipose cell differentiation inducing substances are not particularly limited as long as a substance has an action to differentiate a cell inducible to differentiate into a mature adipocyte or has an assisting action on the action, and examples include one or more substances selected from the group consisting of dexamethasone, isobutylmethylxanthine, insulin, and serum, of which, in light of obtaining a good differentiation inducing efficiency into a mature adipocyte, "combination of serum and dexamethasone", "combinations of adipose cell differentiation inducing substances comprising at least serum and dexamethasone", "combination of serum and isobutylmethylxanthine", and "combinations of adipose cell differentiation inducing substances comprising at least serum and isobutylmethylxanthine" being preferable, of which "combination of serum, dexamethasone, and insulin", "combinations of adipose cell differentiation inducing substances comprising at least serum, dexamethasone, and insulin", "combination of serum, isobutylmethylxanthine, and insulin", "combinations of adipose cell differentiation inducing substances comprising at least serum, isobutylmethylxanthine and insulin", "combination of serum, dexamethasone, and isobutylmethylxanthine", and "combinations of adipose cell differentiation inducing substances comprising at least serum, dexamethasone, and isobutylmethylxanthine" being more preferable, of which "combination of serum, dexamethasone, isobutylmethylxanthine, and insulin", "combinations of adipose cell differentiation inducing substances comprising at least serum, dexamethasone, isobutylmethylxanthine, and insulin" being further preferable. The adipose cell differentiation inducing substances and the basal medium for mesenchymal cell culture comprising such a substance may be commercial products, or a medium prepared by adding an adipose cell differentiation inducing substance to the basal medium for mesenchymal cell culture may be used as such a medium. Examples of the commercial medium comprising an adipose cell differentiation inducing substance preferably include Adipocyte Differentiation Medium (manufactured by Cell Applications, Inc.). Examples of the substance having an assisting action on the action to differentiate into a mature adipocyte other than the above listed adipose cell differentiation inducing substances include Rosiglitazone, Pioglitazone, and Indomethacin.

The concentration of the above adipose cell differentiation inducing substances in the medium is not particularly limited as long as a concentration can induce mesenchymal stem cells into mature adipocytes but examples include, in terms of dexamethasone concentration, typically a range from 0.1 to 10 µM, preferably a range from 0.5 to 2.5 µM, in terms of isobutylmethylxanthine concentration, a range from 10 to 1000 µM, preferably a range from 250 to 750 µM, in terms of insulin concentration, a range from 0.1 to 10 µM, preferably a range from 0.5 to 2.5 µM, and in terms of serum concentration, a range from 1 to 20 wt %, preferably a range from 5 to 15 wt %, more preferably 7 to 13 wt %.

The "basal medium for mesenchymal cell culture" in the present Description is not particularly limited as long as medium can culture at least 1 kind of the mesenchymal cells therein and proliferate the mesenchymal cell, but in light of easy preparation and preventing lot-to-lot variation, a chemically synthesized medium is preferable, and the medium preferably comprises one or more saccharide(s), one or more inorganic salt(s), one or more amino acid(s), and one or more vitamin(s), and one or more other components as needed.

Examples of the above saccharide specifically include a monosaccharide such as glucose, mannose, fructose and galactose, and a disaccharide such as sucrose, maltose, and lactose, of which glucose being particularly preferable, and one or more of these saccharides can be added in combination.

Examples of the above inorganic salt specifically include one or more inorganic salt(s) such as calcium chloride, calcium nitrate, a copper sulfate pentahydrate, an iron(III) nitrate nonahydrate, an iron (II) sulfate heptahydrate, a magnesium chloride hexahydrate, magnesium sulfate, potassium chloride, sodium chloride, sodium bicarbonate, disodium hydrogen phosphate, a disodium hydrogenphosphate dihydrate, sodium dihydrogen phosphate, a sodium dihydrogen phosphate monohydrate, a sodium dihydrogen phosphate dihydrate, a sodium selenite pentahydrate, and a zinc sulfate heptahydrate.

Examples of the above amino acids specifically include one or more amino acid(s) selected from alanine, arginine, asparagine, aspartic acid, cystine, cysteine, glutamine, glycine, histidine, glutamic acid, hydroxyproline, isoleucine, leucine, lysine, methionine, phenylalanine, proline, serine, threonine, tryptophan, tyrosine, and valine, and preferably include an L-form amino acid and a derivative thereof and a by-product such as a salt thereof and a hydrate thereof. Examples of the above arginine include an arginine by-product such as an L-arginine hydrochloride and an L-arginine monohydrochloride, examples of the above aspartic acid include an aspartic acid by-product such as an L-sodium aspartate monohydrate, an L-aspartic acid monohydrate, potassium L-aspartate, and magnesium L-aspartate, examples of the above cysteine include a cysteine by-product such as L-cysteine dihydrochloride and an L-cysteine hydrochloride monohydrate, and a lysine by-product such as L-lysine hydrochloride, examples of the above glutamic acid include a glutamine by-product such as monosodium L-glutamate, examples of the above asparagine include an asparagine by-product such as an L-asparagine monohydrate, examples of the above tyrosine include a tyrosine by-product such as an L-tyrosine disodium dihydrate, examples of the above histidine include a histidine by-product such as histidine hydrochloride and a histidine hydrochloride monohydrate, and examples of the above lysine include a lysine by-product such as L-lysine hydrochloride.

Examples of the above vitamins specifically include one or more vitamin(s) selected from biotin, choline, folic acid, inositol, niacin, pantothenic acid, pyridoxine, riboflavin, thiamine, vitamin B12, paraaminobenzoic acid (PABA), and ascorbic acid, and a derivative each thereof and a by-product thereof such as a salt thereof and a hydrate thereof. Examples of the above choline include a choline by-product such as choline chloride, examples of the niacin include a niacin by-product such as nicotinic acid, nicotinamide, and nicotinic alcohol, examples of the pantothenic acid include a pantothenic acid by-product such as calcium pantothenate, sodium pantothenate, and panthenol, examples of the pyridoxine include a pyridoxine by-product such as pyridoxine hydrochloride, pyridoxal hydrochloride, pyridoxal phosphate, and pyridoxamine, examples of the thiamine include a thiamine by-product such as thiamine hydrochloride, thiamine nitrate, bisthiamine nitrate, a thiamine dicetyl sulfate ester salt, fursultiamine hydrochloride, octothiamine, and benfotiamine, examples of the ascorbic acid include an ascorbic acid by-product such as ascorbic acid 2-phosphate, ascorbic acid magnesium phosphate, sodium ascorbate sulfate, aminopropyl ascorbyl phosphate, and sodium ascorbate phosphate.

Examples of the above other components include a buffer such as HEPES, an antibiotic such as penicillin and streptomycin, pyruvic acid and a derivative thereof and a by-product thereof such as a salt thereof and a hydrate thereof, and phenol red, examples of the above antibiotics include penicillin G sodium and streptomycin sulfate, or preferably a penicillin-streptomycin solution, and examples of the pyruvic acid by-product preferably include sodium pyruvate.

Specific examples of the above basal medium for mesenchymal cell culture include a known commercial chemically synthesized medium such as Dulbecco's modified Eagle's medium (DMEM), Iscove's Modified Dulbecco's Medium (IMDM), RPMI 1640 medium, minimum essential medium (MEM), basal medium of Eagle (BME), and F12 medium, a medium of 2 or more of these medium mixed in a suitable ratio such as DMEM/F12 (medium of DMEM and F12 medium mixed in 1:1), with medium to which one or more substances selected from the group consisting of antibiotics such as penicillin and streptomycin; and additional amino acids (preferably non-essential amino acids); are added being preferable, and medium wherein an antibiotic (preferably penicillin G sodium, streptomycin sulfate or a penicillin-streptomycin solution) is further added to DMEM, IMDM or RPMI 1640 medium being particularly more preferable, of which medium wherein an antibiotic (preferably penicillin G sodium, streptomycin sulfate, or a penicillin-streptomycin solution) is further added to DMEM being particularly preferable.

Examples of the particularly preferable basal medium for mesenchymal cell culture in the present invention include medium wherein 100 U/mL (final concentration) of a penicillin-streptomycin solution is added to DMEM having composition to be described later (hereinafter referred to as "particularly preferable basal medium in the present invention"), and medium comprising each component in a concentration of the proportion ranging independently from 70% to 130% to the concentration of each component in the particularly preferable basal medium in the present invention.

(Composition of DMEM)

200 mg/L of anhydrous calcium chloride, 0.1 mg/L of $Ee(NO_3)_3 \cdot 9H_2O$, 200 mg/L of potassium chloride, 97.67 mg/L of anhydrous magnesium sulfate, 6400 mg/L of sodium chloride, 3700 mg/L of sodium bicarbonate, 125 mg/L of sodium dihydrogen phosphate monohydrate, 4500 mg/L of D-glucose, 15 mg/L of phenol red, 110 mg/L of sodium pyruvate, 84 mg/L of L-arginine hydrochloride, 63 mg/L of L-cysteine dihydrochloride, 584 mg/L of L-glutamine, 30 mg/L of glycine, 42 mg/L of L-histidine hydrochloride monohydrate, 105 mg/L of L-isoleucine, 105 mg/L of L-leucine, 146 mg/L of L-lysine hydrochloride, 30 mg/L of L-methionine, 66 mg/L of L-phenylalanine, 42 mg/L of L-serine, 95 mg/L of L-threonine, 16 mg/L of L-tryptophan, 104 mg/L of L-tyrosine disodium dihydrate, 94 mg/L of L-valine, 4 mg/L of D-calcium pantothenate, 4 mg/L of choline chloride, 4 mg/L of folic acid, 7.2 mg/L of i-inositol, 4 mg/L of nicotinamide, 4 mg/L of pyridoxine hydrochloride, 0.4 mg/L of riboflavin, 4 mg/L of thiamine hydrochloride.

Mature adipocytes obtained in the above step (A) (that is, the mature adipocyte population comprising mature adipocytes) are easy-to-dedifferentiate mature adipocytes, which are comparatively easily dedifferentiated when induced to dedifferentiate (that is, easy-to-dedifferentiate mature adipocyte population comprising easy-to-dedifferentiate mature adipocytes). The "easy-to-dedifferentiate mature adipocyte population" in the present Description means a mature adipocyte population having a proportion of the cell line obtained which is 1.5 or more times more than that of the mature adipocyte population collected from a vertebrate adipose tissue as described in the conventional method (Patent Document 2; Japanese Patent No. 5055611), and includes mature adipocyte populations having preferably 2 or more times, more preferably 4 or more times, further preferably or more times, more preferably 10 or more times, and further preferably 15 or more times proportions. The above "proportion of the cell line obtained" indicates the proportion of cell line obtained from a specific amount of a mature adipocyte population, and the proportion preferably includes, for example, a proportion (rate) of "a weight of a cell line to be obtained" to "a weight of mature adipocytes to be used for dedifferentiation induction."

(Step B)

The above step (B) is not particularly limited as long as a step can induce dedifferentiation of the mature adipocytes (easy-to-dedifferentiate mature adipocytes) obtained in step (A) to obtain a mesenchymal cell line derived from a vertebrate adipose tissue. The step is an ex vivo or in vitro step.

Mature adipocytes used in step (B) is the mature adipocytes obtained by the differentiation induction in step (A). Such mature adipocytes can be obtained by, for example, centrifuging the culture suspension of step (A) and collecting the cells which float in the upper part of supernatant. This is because mature adipocytes comprise a large amount of fats, thus have a light specific gravity and float in the upper part of supernatant when centrifuged.

In the above step (B), the method of inducing dedifferentiation of the mature adipocytes (easy-to-dedifferentiate mature adipocytes) obtained in step (A) to obtain a mesenchymal cell line derived from a vertebrate adipose tissue is not particularly limited as long as a method can induce dedifferentiation of the mature adipocytes to obtain a mesenchymal cell line derived from a vertebrate adipose tissue, but examples preferably include a method of so-called ceiling culture of the mature adipocytes. The ceiling culture is a method for culturing cells by allowing the cells to adhere or float (preferably allowed to adhere) to the inner upper surface (ceiling surface) of a culture vessel (preferably a culture flask) filled up with medium, and this method for culturing cells utilizes the property of mature adipocytes which comprise a large amount of fats, thus have a light specific gravity and float in the medium.

Examples of the medium when carrying out the dedifferentiation inducing culture of a mature adipocyte include basal medium for mesenchymal cell culture comprising the extracellular matrix, and examples of the extracellular matrix include one or more components selected from collagen, fibronectin, proteoglycan, laminin, and serum (FBS), and BD Matrigel (registered trademark) (manufactured by BD Biosciences) comprising such a component can also be used. Serum such as FBS in medium when carrying out the dedifferentiation inducing culture of a mature adipocyte may be used only as an adhesion factor for allowing a mature adipocyte to adhere to the ceiling surface of a culture vessel or may not be used only as the adhesion factor for that purpose. The medium when carrying out the dedifferentiation inducing culture of a mature adipocyte may not comprise serum such as FBS, but in light of producing a mesenchymal cell line derived from a vertebrate adipose tissue more efficiently, it is preferable to comprise serum such as FBS with the extracellular matrix other than serum or without the extracellular matrix other than serum. The serum concentration, in the case where the medium comprises serum such as FBS, is not particularly limited as long as a mesenchymal cell line derived from a vertebrate adipose tissue is obtained but examples include a range from 3 to 30 wt %, preferably include a range from 7 to 25 wt %, more preferably include a range from 7 to 13 wt %.

In the above step (B), when the conditions, other than the ceiling culture conditions, for culturing a mature adipocyte in the basal medium for mesenchymal cell culture comprising the extracellular matrix are described, examples of the culture temperature typically include a range from 12 to 45° C., preferably a range from 15 to 37° C., and examples of the culture period include a range from 2 to 28 days, preferably a range from 4 to 21 days, more preferably a range from 5 to 14 days, further preferably a range from 6 to 10 days, more preferably for 7 days, in light of balancing the production of a mesenchymal cell line derived from a vertebrate adipose tissue between more efficiently and in a shorter period of time. In the culture, a mature adipocyte may or may not be subcultured.

A mesenchymal cell line derived from a vertebrate adipose tissue may or may not be isolated from the medium after the ceiling culture in the above step (B), but it is preferable to isolate. When the ceiling culture is continued, mature adipocytes gradually decrease while the established mesenchymal cell line derived from an adipose tissue actively proliferates and a cell population comprising a large amount of mesenchymal cell lines derived from an adipose tissue can be obtained. For example, when the ceiling culture is continued for about 14 days, a cell population containing an extremely large amount of mesenchymal cell lines derived from an adipose tissue can be obtained.

The ceiling culture in the above step (B) include, for the sake of convenience, the continuation of culture in which after the mature adipocyte (easy-to-dedifferentiate mature adipocyte) obtained in step (A) is adhered to the ceiling surface of a culture vessel, the culture vessel is arranged in such a way that the adhesion surface turns to the bottom side thereof, however, the culture may be continued while the mature adipocyte (easy-to-dedifferentiate mature adipocyte) obtained in step (A) are adhered to the ceiling surface of a culture vessel to obtain a mesenchymal cell derived from an adipose tissue without carrying out the culture in which the culture vessel is arranged in such a way that the adhesion surface turns to the bottom side of the medium.

<Mesenchymal Cell Line Derived from Vertebrate Adipose Tissue>

The mesenchymal cell line derived from a vertebrate adipose tissue of the present invention is not particularly limited as long as a mesenchymal cell line derived from a vertebrate adipose tissue is produced by the method for producing a cell line of the present invention. The mesenchymal cell line derived from a vertebrate adipose tissue of the present invention does not spontaneously differentiate when cultured in the typical basal medium for mesenchymal cell culture which does not have a differentiation inducing action, is suitable for long-term subculture, and maintains proliferation potency and differentiation potency into mesodermal cells (one or more selected from the group consisting of a megakaryocyte/platelet, an osteoblast, a cartilage, and an adipocyte) even after long-term subculture. For example, the mesenchymal cell line derived from an adipose tissue of the present invention produced from a human subcutaneous adipose tissue has been observed to maintain proliferation potency even in the 20th generation and have a doubling time of 23 hours.

The mesenchymal cell line derived from a vertebrate adipose tissue of the present invention has a notably higher differentiation inducing efficiency into mesodermal cells (preferably megakaryocytes/platelets) than the mesenchymal cell line derived from an adipose tissue produced by the conventional method (Patent Document 2; Japanese Patent No. 5055611). For this reason, the mesenchymal cell line derived from a vertebrate adipose tissue of the present invention can also be said to be the mesenchymal cell line derived from an adipose tissue easily inducible to differentiate into mesodermal cells (easily differentiation inducible mesenchymal cell line derived from an adipose tissue). The "easily differentiation inducible mesenchymal cell line derived from an adipose tissue" in the present Description means the mesenchymal cell line, derived from an adipose tissue, having a differentiation inducing efficiency into any one of the mesodermal cells (preferably megakaryocytes/platelets) which is 1.5 or more times more than that of the mesenchymal cell line derived from an adipose tissue produced by the convention method (Patent Document 2; Japanese Patent No. 5055611), and includes mesenchymal cell lines derived from an adipose tissue having a differentiation inducing efficiency of preferably or more times, more preferably 2.5 or more times, further preferably 3 or more times.

The mesenchymal cell line derived from a vertebrate adipose tissue of the present invention preferably expresses one or more (preferably 3 or more, more preferably 5 or more, further preferably 7 or more, more preferably 8 or 9, most preferably 9) surface markers selected from the following surface marker group of mesenchymal cells, and does not express one or more (preferably 3 or more, more preferably 5 or more, further preferably 7 or more, more preferably 8 or 9, most preferably 9) surface markers selected from the following surface marker group of blood cells.

Surface marker group of mesenchymal cells: CD13, CD29, CD44, CD71, CD73, CD90, CD105, CD166, HLA-ABC;
Surface marker group of blood cells: CD11b, CD14, CD19, CD34, CD41, CD42b, CD45, CD56, HLA-DR;

International Society for Cellular Therapy sets conditions to define the mesenchymal stem cell as (A) to be an adherent cell, (B) to be capable of differentiating into bones, cartilages, and fats, and (C) to express surface markers of mesenchymal cells and not express surface markers of blood cells. Of the mesenchymal cell lines derived from a vertebrate adipose tissue of the present invention, the cell lines of a preferable embodiment meet the conditions (A), (B), and (C).

<Method for Producing Mesodermal Cells>

The method for producing mesodermal cells of the present invention is not particularly limited as long as a method has a step of inducing a mesenchymal cell line derived from a vertebrate adipose tissue to differentiate into a mesodermal cell to obtain a mesodermal cell. Examples of the mesodermal cells include a megakaryocyte and/or a platelet (megakaryocytes/platelets), an osteoblast, a cartilage, and an adipocyte.

For the method for inducing differentiation of the mesenchymal cell line derived from a vertebrate adipose tissue of the present invention into a mesodermal cell, a known method for inducing differentiation of mesenchymal cells into a mesodermal cell can be used, and examples include a method in which the mesenchymal cell line derived from a vertebrate adipose tissue of the present invention is cultured in the basal medium for mesenchymal cell culture comprising substances known to have a differentiation inducing action into respective kind of a mesodermal cell.

Examples of the medium having a differentiation inducing action into megakaryocytes/platelets include MKLI medium (megakaryocyte lineage induction medium)(Non-patent Document 5) and basal medium for mesenchymal cell culture comprising iron ions and iron transporters (Patent Document 1) (preferably the basal medium for mesenchymal cell culture comprising iron-bound transferrin; Patent document 1). Further, examples of the medium having a differentiation inducing action into an osteoblast include basal medium for mesenchymal cell culture (International Publication No. WO 2012/029863) comprising hydrocortisone, dexamethasone, and serum, and examples of the commercial osteoblast differentiation inducing medium include Osteoblast Differentiation Medium manufactured by Cell Applications, Inc. Additionally, examples of the medium having a differentiation inducing action into a cartilage include basal medium for mesenchymal cell culture comprising a transforming growth factor β3 (TGF-β3), dexamethasone, and serum, and examples of the commercial cartilage differentiation inducing medium include hMSC Mesenchymal Stem Cell Chondrocyte Differentiation Medium manufactured by Lonza. Further, examples of the medium having a differentiation inducing action into adipocytes include, as described earlier, basal medium for mesenchymal cell culture comprising one or more adipose cell differentiation inducing substances selected from the group consisting of dexamethasone, isobutylmethylxanthine, insulin, and serum, and examples of the commercial adipocyte differentiation inducing medium include Adipocyte Differentiation Medium manufactured by Cell Applications, Inc.

The present invention will be hereinafter described in detail in reference with Examples but not limited thereto. The concentrations of medium components described in the following Examples all indicate final concentrations in the medium.

EXAMPLE 1

[Preparation of Mesenchymal Cell Line Derived from Adipose Tissue]

After isolating a piece of subcutaneous adipose tissue from human, collagenase (collagenase type II; manufactured by Sigma-Aldrich) was added and the tissue was incubated at 37° C. for 1 hour, thereby obtaining a cell suspension. When the cell suspension was centrifuged, the mature adipocytes having a light specific gravity floated in the supernatant and other kinds of cells precipitated as a cell pellet. The cell pellet comprised mesenchymal stem cells, adipose progenitor cells, stromal cells (stroma cells), vascular endothelial cells, smooth muscle cells, and fibroblasts. The cells in the cell pellet were used in the subsequent experiments. The cells in the above cell pellet were cultured under the conditions of 37° C. and 5% $CO_2$ for 10 days in Adipocyte Differentiation Medium (manufactured by Cell Applications, Inc.) in a culture dish. The cultured cells comprised a large number of mature adipocytes (easy-to-dedifferentiate mature adipocytes) induced to differentiate from a stromal vascular fraction comprising mesenchymal stem cells, adipose progenitor cells, and stromal cells. The cultured cells were detached using trypsin from the culture dish, trypsin and DMEM (Dulbecco's Modified Eagle's Medium, manufactured by Life Technology, Inc.) were added to the cells and centrifuged, whereby the mature adipocytes (easy-to-dedifferentiate mature adipocytes) floated in the supernatant were recovered. The easy-to-dedifferentiate mature adipocytes described above were added to a culture flask in which an adequate amount of DMEM comprising 20% FBS was added, and the cells were cultured while allowed to float and adhere to the upper surface of the inner side of the culture flask filled up with the medium (so-called "ceiling culture"). The ceiling culture was carried out under the conditions of 37° C. and 5% $CO_2$ for 7 days. The culture thus carried out enabled to obtain a mesenchymal cell line derived from a human adipose tissue. FIG. 1 shows the observation result of the mesenchymal cell line derived from a human adipose tissue using a phase-contrast microscopy. As evident in FIG. 1, the cell line was in the fibroblast-like form and was confirmed to proliferate while adhering to the culture dish. International Society for Cellular Therapy sets conditions to define the mesenchymal stem cell as (A) to be an adherent cell, (B) to be capable of differentiating into bones, cartilages, and fats, and (C) to express surface markers of mesenchymal cells and not express surface markers of blood cells. The result shown in FIG. 1 revealed that the mesenchymal cell line derived from a human adipose tissue in the present invention satisfied (A) among the above definition conditions to be the mesenchymal cell.

In the conventional method (Patent Document 2), it took a period of more than about 2 months to prepare an adipose progenitor cell line from the collection of an adipose tissue, however, in the method of the present invention, a large amount of a mesenchymal cell line derived from an adipose tissue was prepared from the collection of the adipose tissue in less than 1 month. The obtained mesenchymal cell line derived from a human adipose tissue was subcultured in DMEM comprising 10% FBS (basal medium for adipose progenitor cell culture).

When the method of the present invention (a method of establishing a cell line by preparing easy-to-dedifferentiate mature adipocytes and subjecting the cells to the ceiling culture) and the conventional method (a method of establishing a cell line by subjecting mature adipocytes collected from an adipose tissue to the ceiling culture (Patent Document 2; Japanese Patent No. 5055611)) were compared on the amount of cell line (the number of cells) obtained in the same preparation period (for example, 2 months) in the case of preparing an adipose progenitor cell line from a piece of subcutaneous adipose tissue of the same size (1 square cm), the cell line was obtained in about 15 times as much as the conventional method in the present invention. This confirmed that the method for producing a mesenchymal cell line derived from a vertebrate adipose tissue (establishment method) of the present invention can produce a mesenchymal cell line from a vertebrate adipose tissue notably more efficiently. Further, it was observed that the obtained mesenchymal cell line derived from a human adipose tissue maintained proliferation potency even in the 20th generation and had a doubling time of 23 hours.

A human subcutaneous adipose tissue was used in Example 1, but the present inventors confirmed that a mesenchymal cell line derived from an adipose tissue can also be obtained by the same method in the case where a mouse subcutaneous adipose tissue was used.

EXAMPLE 2

[Induction of Differentiation of Mesenchymal Cell Line Derived from Adipose Tissue into Osteoblasts]

The mesenchymal cell line derived from a human adipose tissue obtained in the above Example 1 was cultured in osteoblast differentiation inducing medium (manufactured by Cell Applications, Inc.) in a culture dish under the conditions of 37° C. and 5% $CO_2$ for 21 days. When the alkaline phosphatase activity of the obtained cells was confirmed by adding bromochloroindolyl phosphate/nitro blue tetrazolium, the substrate thereof, the color development of bluish purple color (but appeared as a blackish color in the drawing) was recognized (FIG. 2, right panel in the first row from the top). This verified the differentiation into osteoblasts.

Further, when the cultured cells described above were stained with Alizarin red to confirm the calcification of cells, the color development of red color (but appeared as a blackish color in the drawing) was recognized (FIG. 2, right panel in the second row from the top). This verified the calcification of osteoblasts.

The above results verified that the mesenchymal cell line derived from a vertebrate adipose tissue produced by the production method of the present invention had differentiation potency into osteoblasts.

A mesenchymal cell line derived from a human adipose tissue was used in Example 2, but the present inventors confirmed that the differentiation potency into osteoblasts was also maintained in the case where a mesenchymal cell line derived from a mouse adipose tissue was used.

EXAMPLE 3

[Induction of Differentiation of Mesenchymal Cell Line Derived from Adipose Tissue into Adipocytes]

The mesenchymal cell line derived from a human adipose tissue obtained in the above Example 1 was cultured in Adipocyte Differentiation Medium (manufactured by Cell Applications, Inc.) in a culture dish under the conditions of 37° C. and 5% $CO_2$ for 7 days. When the obtained cells were stained with oil red O to confirm the presence of fat globules, the color development of red color (but appeared as a blackish color in the drawing) was recognized (FIG. 2, right panel in the third row from the top). This verified the differentiation into mature adipocytes. This verified that the mesenchymal cell line derived from a vertebrate adipose tissue produced by the production method of the present invention had differentiation potency into adipocytes.

A mesenchymal cell line derived from a human adipose tissue was used in Example 3, but the present inventors confirmed that the differentiation potency into adipocytes was also maintained in the case where a mesenchymal cell line derived from a mouse adipose tissue was used.

EXAMPLE 4

[Induction of Differentiation of Mesenchymal Cell Line Derived from Adipose Tissue into Chondrocytes]

The mesenchymal cell line derived from a human adipose tissue obtained in the above Example 1 was cultured in Chondrogenic Differentiation Medium (manufactured by PromoCell) in a culture dish under the conditions of 37° C. and 5% $CO_2$ for 7 days. When the obtained cells were stained with Alcian blue to confirm the presence of extracellular matrix distinctive in chondrocytes, the color development of blue color (but appeared as a blackish color in the drawing) was recognized (FIG. 2, right panel in the third row from the top). This verified the differentiation into chondrocytes. This verified that the mesenchymal cell line derived from a vertebrate adipose tissue produced by the production method of the present invention had differentiation potency into chondrocytes.

The results of the above Examples 3 and 4 revealed that mesenchymal cell line derived from a human adipose tissue obtained in the above Example 1 satisfied the condition "(B) to be capable of differentiating into bones, cartilages, and fats" as defined to be the mesenchymal stem cell set by International Society for Cellular Therapy.

EXAMPLE 5

[Expression of Surface Markers of Mesenchymal Cells and Blood Cells in Mesenchymal Cell Line Derived from Adipose Tissue]

To investigate whether the mesenchymal cell line derived from a human adipose tissue obtained in the above Example 1 satisfied the condition "(C) to express surface markers of mesenchymal cells and not express surface markers of blood cells" as defined to be the mesenchymal stem cell set by International Society for Cellular Therapy, the expression of each surface marker in the above cells was analyzed by the flow cytometry method using antibodies specific to surface markers of mesenchymal cells (CD13, CD29, CD44, CD71, CD73, CD90, CD105, CD166, HLA-ABC) and surface markers of blood cells (CD11b, CD14, CD19, CD34, CD41, CD42b, CD45, CD56, HLA-DR). Further, as negative controls, the same flow cytometry method was carried out using isotype control antibodies. Of the antibodies specific to surface markers, anti-CD29 antibody, anti-CD42b antibody, and anti-CD71 antibody used were products of BD Pharmingen, anti-CD105 antibody used was a product of Beckman Coulter, Inc., and other antisurface marker antibodies were products of BioLegend, Inc. FIG. 3 shows the results of the flow cytometry described above.

As shown in each panel in the lower row of FIG. 3, the surface markers of blood cells had no signal differences between the case where the surface marker antibodies were used and the case where isotype control antibodies were used. On the other hand, as shown in each panel in the upper row of FIG. 3, the surface markers of mesenchymal cells had intense fluorescent signals when the case where the surface marker antibodies were used was compared with the case where isotype control antibodies were used. These results revealed that the mesenchymal cell line derived from a human adipose tissue obtained in the above Example satisfied the condition "(C) to express surface markers of mesenchymal cells and not express surface markers of blood cells" as defined to be the mesenchymal stem cell set by International Society for Cellular Therapy.

The results of the above Examples 1 to 5 verified that the mesenchymal cell line derived from a human adipose tissue obtained in the above Example 1 satisfied all 3 conditions (A) to be an adherent cell, (B) to be capable of differentiating into bones, cartilages, and fats, and (C) to express surface markers of mesenchymal cells and not express surface markers of blood cells as defined to be the mesenchymal stem cell set by International Society for Cellular Therapy.

EXAMPLE 6

[Induction of Mesenchymal Cell Line Derived from Adipose Tissue to Differentiate into Megakaryocytes and/or Platelets]

A culture dish was coated with collagen and culture medium was added thereto. The culture medium used was MKLI medium (megakaryocyte lineage induction medium) known as the medium capable of inducing hematopoietic stem cells to differentiate into megakaryocytes and platelets. The MKLI medium was prepared by adding, to IMDM (Iscove's Modified Dulbecco's Medium, manufactured by Life Technology, Inc.), 2 mM of L-glutamine (manufactured by Life Technology, Inc.), 100 U/mL of a penicillin-streptomycin solution (manufactured by Life Technology, Inc.), 0.5% BSA (manufactured by Sigma-Aldrich), 4 µg/mL of LDL cholesterol (manufactured by Sigma-Aldrich), 200 µg/mL of iron-saturated transferrin (manufactured by Sigma-Aldrich), 10 µg/mL of insulin (manufactured by Sigma-Aldrich), 50 µM of 2-β-mercaptoethanol (manufactured by Life Technology, Inc.), 20 µM of each nucleotide (ATP, UTP, GTP, and CTP) (manufactured by Life Technology, Inc.), and 50 ng/mL of human thrombopoietin (TPO, manufactured by Stem Cell Technologies).

(Confirmation of Specific Markers CD41 and CD42b)

The mesenchymal cell line derived from a human adipose tissue obtained in the above Example 1 was cultured in the above MKLI medium under the conditions of 37° C. and 5% $CO_2$ for 7 days. After fractionating the cultured cell population, CD41 and CD42b (specific markers to megakaryocytes and platelets) in the cell population were measured for proportion (%) of positive cells. FIG. 4 shows the results. The measurement was carried out by the flow cytometry method by directly labeling the cells with FITC (fluorescein isothiocyanate)-labeled anti-CD41 antibody or APC (allophycocyanin)-labeled anti-CD42b antibody. In the cell population, the proportion of the CD41 positive cells was 70.4±3.9% and the proportion of the CD41 positive and CD42b positive cells was 23.6±2.4%.

(Confirmation on DNA Ploidy)

Megakaryocytes are known to increase the DNA ploidy when the differentiation proceeds. Accordingly, the cell population obtained by culturing a mesenchymal cell line derived from a human adipose tissue in MKLI medium under the conditions of 37° C. and 5% $CO_2$ for 7 days was measured for the DNA ploidy by the method of Hagiwara et al. (Exp. Hematol., 26, 228 to 235, 1998). That is, nuclei of the cells in the cell population described above were stained with Propidium iodide (PI) and subsequently the fluorescence intensity of PI in each cell was measured by the flow cytometry method to calculate a DNA ploidy of each cell. FIG. 5 shows the results. As evident in FIG. 5, polyploid cells such as 4N and 8N were recognized.

(Confirmation on Platelet Function by Stimulation)

Fibrinogen in platelets contributes to the actions such as blood coagulation and PAC-1 is a platelet-activating marker. To confirm whether the cell population obtained by culturing a mesenchymal cell line derived from a human adipose tissue in MKLI medium under the conditions of 37° C. and 5% $CO_2$ for 7 days had the platelet function, the expressions of fibrinogen and PAC-1 were measured. The measurement was carried out by the flow cytometry method by directly labeling the cells with FITC (fluorescein isothiocyanate)-labeled anti-fibrinogen antibody or FITC-labeled anti-PAC-1 antibody. Further, as controls, the same flow cytometry method was carried out on a mesenchymal cell line derived from a human adipose tissue before starting the culture in MKLI medium. FIG. 6 shows the result of the flow cytometry method using the FITC-labeled anti-fibrinogen antibody, and FIG. 7 shows the result of the flow cytometry method using the FITC-labeled anti-PAC-1 antibody. As evident in FIG. 6 and Figure cell population obtained by culturing a mesenchymal cell line derived from a human adipose tissue in MKLI medium had increased expressions of fibrinogen and PAC-1.

The above results confirmed the differentiation of the mesenchymal cell line derived from a human adipose tissue into megakaryocytes/platelets. This verified that the mesenchymal cell line derived from a vertebrate adipose tissue produced by the production method of the present invention had differentiation potency into megakaryocytes/platelets.

A mesenchymal cell line derived from a human adipose tissue was used in Example 6, but the present inventors confirmed that the differentiation potency into megakaryocytes/platelets was also maintained in the case where a mesenchymal cell line derived from a mouse adipose tissue was used.

EXAMPLE 7

[Comparison on Yield with Conventional Method (Patent Document 2)]

A mesenchymal cell line derived from a human adipose tissue was prepared in accordance with the method described in Patent Document 2 (hereinafter referred to as "the mesenchymal cell line derived from an adipose tissue according to the convention method). Separately, the mesenchymal cell line derived from a human adipose tissue produced in Example 1 (hereinafter referred to as "the mesenchymal cell line derived from an adipose tissue according to the present invention") was provided. The same amount of each of these 2 types of mesenchymal cell lines derived from an adipose tissue was fractionated, cultured respectively in MKLI medium under the conditions of 37° C. and 5% $CO_2$ for 7 days to induce the differentiation into megakaryocytes/platelets. After fractionating the cultured cell population, CD41 and CD42b (specific markers to megakaryocytes and platelets) in the cell population were measured for proportion m of positive cells. As a result, when the mesenchymal cell line derived from an adipose tissue according to the present invention was used, the positive cells of CD41 and CD42b (specific markers to megakaryocytes and platelets) were obtained 3 times as much compared with the case of using the same amount of the mesenchymal cell line derived from an adipose tissue according to the conventional method. The above result revealed that the mesenchymal cell line derived from an adipose tissue according to the present invention was a cell line having as high as 3 times an inducing efficiency into megakaryocytes/platelets compared with the mesenchymal cell line derived from an adipose tissue according to the conventional method.

INDUSTRIAL APPLICABILITY

According to the present invention, a method for producing a mesenchymal cell line derived from a vertebrate adipose tissue and a mesenchymal cell line derived from a vertebrate adipose tissue produced by the production method can be provided. More specifically, the present invention can provide a method for producing a mesenchymal cell line derived from a vertebrate adipose tissue more simply, in a shorter period of time, and more efficiently and a mesenchymal cell line derived from a vertebrate adipose tissue produced by the production method.

The invention claimed is:

1. A mesenchymal cell line obtained from vertebrate adipose tissue produced by a production method for producing a mesenchymal cell line obtained from vertebrate adipose tissue, the production method comprising the following steps (A) and (B):
   (A) obtaining a large number of mature adipocytes by isolating a piece of subcutaneous vertebrate adipose tissue, digesting said adipose tissue to obtain a cell suspension, precipitating by centrifugation the cell suspension and thereby causing mature adipocytes to float in the supernatant, and culturing a digested pellet comprising stromal vascular cells obtained from vertebrate adipose tissue for 10 days in adipocyte differentiation medium; and
   (B) inducing dedifferentiation of the mature adipocyte obtained in step (A) to obtain a mesenchymal cell line obtained from the vertebrate adipose tissue, wherein the mesenchymal cell line has a differentiation inducing efficiency into a mesodermal cell which is 1.5 or more times more than that of a mesenchymal cell line obtained from a vertebrate adipose tissue obtained by inducing dedifferentiation of a mature adipocyte collected from a vertebrate adipose tissue.

2. The mesenchymal cell line obtained from a vertebrate adipose tissue according to claim 1, wherein the mesenchymal cell line has a differentiation potency into one or more selected from the group consisting of a megakaryocyte/platelet, an osteoblast, a cartilage, and an adipocyte.

3. The mesenchymal cell line obtained from a vertebrate adipose tissue according to claim 1, wherein the mesenchymal cell line expresses one or more surface markers selected from the following surface marker group of mesenchymal cells, and does not express one or more surface markers selected from the following surface marker group of blood cells:
   surface marker group of mesenchymal cells: CD73, CD90, CD105;
   surface marker group of blood cells: CD11b, CD14, CD19, CD34, CD45, HLA-DR.

4. The mesenchymal cell line obtained from a vertebrate adipose tissue according to claim 1, comprising a step of inducing differentiation of the mesenchymal cell line isolated from a vertebrate adipose tissue into a mesodermal cell, to thereby obtain a mesodermal cell.

5. The mesenchymal cell line obtained from a vertebrate adipose tissue according to claim 4, wherein the mesodermal cell is a megakaryocyte/platelet, an osteoblast, a cartilage, or an adipocyte.

6. The mesenchymal cell line obtained from a vertebrate adipose tissue according to claim 1, wherein the cell population is a cell population obtained by removing the mature adipocyte from a cell population obtained by digesting the vertebrate adipose tissue with an enzyme capable of dispersing the vertebrate adipose tissue cells.

7. The mesenchymal cell line obtained from a vertebrate adipose tissue according to claim 6, wherein the cell population obtained by removing the mature adipocyte from the cell population obtained by digesting the vertebrate adipose tissue with an enzyme capable of dispersing the vertebrate adipose tissue cells is a cell population that is precipitated by centrifugation of a suspension comprising the cell population obtained by digesting the vertebrate adipose tissue with an enzyme capable of dispersing the vertebrate adipose tissue cells.

8. The mesenchymal cell line obtained from a vertebrate adipose tissue according to claim 1, wherein the adipocyte differentiation medium is basal medium for mesenchymal cell culture comprising one or more adipose cell differentiation inducing substances selected from the group consisting of dexamethasone, isobutylmethylxanthine, insulin, and serum.

9. The mesenchymal cell line obtained from a vertebrate adipose tissue according to claim 1, wherein inducing dedifferentiation of the mature adipocyte in step (B) includes performing ceiling culture of the mature adipocyte.

10. The mesenchymal cell line obtained from a vertebrate adipose tissue according to claim 6, wherein the enzyme capable of dispersing the vertebrate adipose tissue cells is one or more enzymes selected from the group consisting of collagenase, trypsin, caseinase, clostripain, trypsin-EDTA, dispase, thermolysin, pronase, hyaluronidase, pancreatin, elastase, and papain.

11. The mesenchymal cell line obtained from a vertebrate adipose tissue according to claim 1, wherein the vertebrate is a mammal.

12. The mesenchymal cell line obtained from a vertebrate adipose tissue according to claim 1, wherein the adipose tissue is a subcutaneous adipose tissue.

13. The mesenchymal cell line obtained from a vertebrate adipose tissue according to claim 6, wherein the step of inducing differentiation of the cell population into a mature adipocyte in step (A) is a step of culturing the cell population in basal medium for mesenchymal cell culture comprising one or more adipose cell differentiation inducing substances selected from the group consisting of dexamethasone, isobutylmethylxanthine, insulin, and serum.

14. The mesenchymal cell line obtained from a vertebrate adipose tissue according to claim 6, wherein inducing dedifferentiation of the mature adipocyte in step (B) includes performing ceiling culture of the mature adipocyte.

15. The mesenchymal cell line obtained from a vertebrate adipose tissue according to claim 7, wherein inducing dedifferentiation of the mature adipocyte in step (B) includes performing ceiling culture of the mature adipocyte.

16. The mesenchymal cell line obtained from a vertebrate adipose tissue according to claim 8, wherein inducing dedifferentiation of the mature adipocyte in step (B) includes performing ceiling culture of the mature adipocyte.

17. The mesenchymal cell line obtained from a vertebrate adipose tissue according to claim 13, wherein inducing dedifferentiation of the mature adipocyte in step (B) includes performing ceiling culture of the mature adipocyte.

18. A method for producing a mesenchymal cell line isolated from a vertebrate adipose tissue, comprising the following steps (A) and (B):

(A) obtaining a large number of mature adipocytes by isolating a piece of subcutaneous vertebrate adipose tissue, digesting said adipose tissue to obtain a cell suspension, precipitating by centrifugation the cell suspension and thereby causing mature adipocytes to float in the supernatant, and culturing the digested pellet comprising stromal vascular cells obtained from vertebrate adipose tissue for 10 days in adipocyte differentiation medium; and (B) inducing dedifferentiation of the mature adipocyte obtained in step (A) to obtain a mesenchymal cell line isolated from the vertebrate adipose tissue, wherein the mesenchymal cell line has a differentiation inducing efficiency into a mesodermal cell which is 1.5 or more times more than that of a mesenchymal cell line obtained from a vertebrate adipose tissue obtained by inducing dedifferentiation of a mature adipocyte collected from a vertebrate adipose tissue.

19. The method for producing a mesenchymal cell line isolated from a vertebrate adipose tissue according to claim 18, wherein the cell population is a cell population obtained by removing the mature adipocyte from a cell population obtained by digesting the vertebrate adipose tissue with an enzyme capable of dispersing the vertebrate adipose tissue cells.

20. The method for producing a mesenchymal cell line isolated from a vertebrate adipose tissue according to claim 19, wherein the cell population obtained by removing the mature adipocyte from the cell population obtained by digesting the vertebrate adipose tissue with an enzyme capable of dispersing the vertebrate adipose tissue cells is a cell population that is precipitated by centrifugation of a suspension comprising the cell population obtained by digesting the vertebrate adipose tissue with an enzyme capable of dispersing the vertebrate adipose tissue cells.

21. The method for producing a mesenchymal cell line isolated from a vertebrate adipose tissue according to claim 18, wherein the step of obtaining the large number of mature adipocytes in step (A) is a step of culturing the cell population in basal medium for mesenchymal cell culture comprising one or more adipose cell differentiation inducing substances selected from the group consisting of dexamethasone, isobutylmethylxanthine, insulin, and serum.

22. The method for producing a mesenchymal cell line isolated from a vertebrate adipose tissue according to claim 18, wherein inducing dedifferentiation of the mature adipocyte in step (B) includes performing ceiling culture of the mature adipocyte.

23. The method for producing a mesenchymal cell line isolated from a vertebrate adipose tissue according to claim 19, wherein the enzyme capable of dispersing the vertebrate adipose tissue cells is one or more enzymes selected from the group consisting of collagenase, trypsin, caseinase, clostripain, trypsin-EDTA, dispase, thermolysin, pronase, hyaluronidase, pancreatin, elastase, and papain.

24. The method for producing a mesenchymal cell line isolated from a vertebrate adipose tissue according to claim 18, wherein the vertebrate is a mammal.

25. The method for producing a mesenchymal cell line isolated from a vertebrate adipose tissue according to claim 19, wherein the step of obtaining the large number of mature adipocytes in step (A) is a step of culturing the cell population in basal medium for mesenchymal cell culture comprising one or more adipose cell differentiation inducing substances selected from the group consisting of dexamethasone, isobutylmethylxanthine, insulin, and serum.

26. The method for producing a mesenchymal cell line isolated from a vertebrate adipose tissue according to claim 20, wherein the step of obtaining large number of mature adipocytes in step (A) is a step of culturing the cell population in basal medium for mesenchymal cell culture comprising one or more adipose cell differentiation inducing substances selected from the group consisting of dexamethasone, isobutylmethylxanthine, insulin, and serum.

27. The method for producing a mesenchymal cell line isolated from a vertebrate adipose tissue according to claim 19, wherein inducing dedifferentiation of the mature adipocyte in step (B) includes performing ceiling culture of the mature adipocyte.

28. The method for producing a mesenchymal cell line isolated from a vertebrate adipose tissue according to claim 20, wherein inducing dedifferentiation of the mature adipocyte in step (B) includes performing ceiling culture of the mature adipocyte.

29. The method for producing a mesenchymal cell line isolated from a vertebrate adipose tissue according to claim 21, wherein inducing dedifferentiation of the mature adipocyte in step (B) includes performing ceiling culture of the mature adipocyte.

30. The method for producing a mesenchymal cell line isolated from a vertebrate adipose tissue according to claim 25, wherein inducing dedifferentiation of the mature adipocyte in step (B) includes performing ceiling culture of the mature adipocyte.

* * * * *